United States Patent
Dafinger et al.

(10) Patent No.: US 9,561,997 B2
(45) Date of Patent: Feb. 7, 2017

(54) PROCESS FOR PREPARING VINYL ACETATE WITH INHIBITED BY-PRODUCT FORMATION

(71) Applicant: WACKER CHEMIE AG, München (DE)

(72) Inventors: Willibald Dafinger, Röhrnbach (DE); Marc Eckert, Calvert City, KY (US)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 15/101,764

(22) PCT Filed: Dec. 2, 2014

(86) PCT No.: PCT/EP2014/076210
§ 371 (c)(1),
(2) Date: Jun. 3, 2016

(87) PCT Pub. No.: WO2015/082450
PCT Pub. Date: Jun. 11, 2015

(65) Prior Publication Data
US 2016/0311752 A1 Oct. 27, 2016

(30) Foreign Application Priority Data
Dec. 6, 2013 (DE) .................. 10 2013 225 114

(51) Int. Cl.
C07C 67/04 (2006.01)
C07C 67/62 (2006.01)

(52) U.S. Cl.
CPC .............. *C07C 67/04* (2013.01); *C07C 67/62* (2013.01)

(58) Field of Classification Search
CPC ...................................... C07C 67/62
See application file for complete search history.

(56) References Cited

U.S. PATENT DOCUMENTS

| 3,467,696 A | 9/1969 | Naito et al. |
| 6,143,205 A | 11/2000 | Sutoris et al. |
| 6,200,460 B1 | 3/2001 | Sutoris et al. |

FOREIGN PATENT DOCUMENTS

| DE | 1244161 B | 7/1967 |
| DE | WO 2010/149527 A1 * | 12/2010 |
| EP | 0567010 A2 | 10/1993 |
| EP | 0791573 A1 | 8/1997 |
| EP | 1233937 B1 | 8/2002 |
| KR | 10-2008-0097529 A | 11/2008 |
| WO | 9746504 A1 | 12/1997 |
| WO | 9825872 A1 | 6/1998 |
| WO | 2007/045886 A1 | 4/2007 |
| WO | 2010149527 A1 | 12/2010 |
| WO | 2012/058196 1 A | 5/2012 |

OTHER PUBLICATIONS

International Search Report for PCT International Application No. PCT/EP2014/076210 dated Feb. 25, 2015.

* cited by examiner

*Primary Examiner* — Paul A Zucker
(74) *Attorney, Agent, or Firm* — RatnerPrestia

(57) ABSTRACT

The invention provides a process for preparing vinyl acetate in a heterogeneously catalyzed, continuous gas phase process by reacting ethylene with acetic acid and oxygen and subsequently working up the product gas stream, with inhibition of the polymerization of vinyl acetate during the workup of the product gas mixture by addition of one or more N-oxyl compounds which contain at least one N-oxyl radical group —N—O. as inhibitors which comprises adding the N-oxyl compound as a 50 to 85% by weight strength aqueous solution.

7 Claims, 1 Drawing Sheet

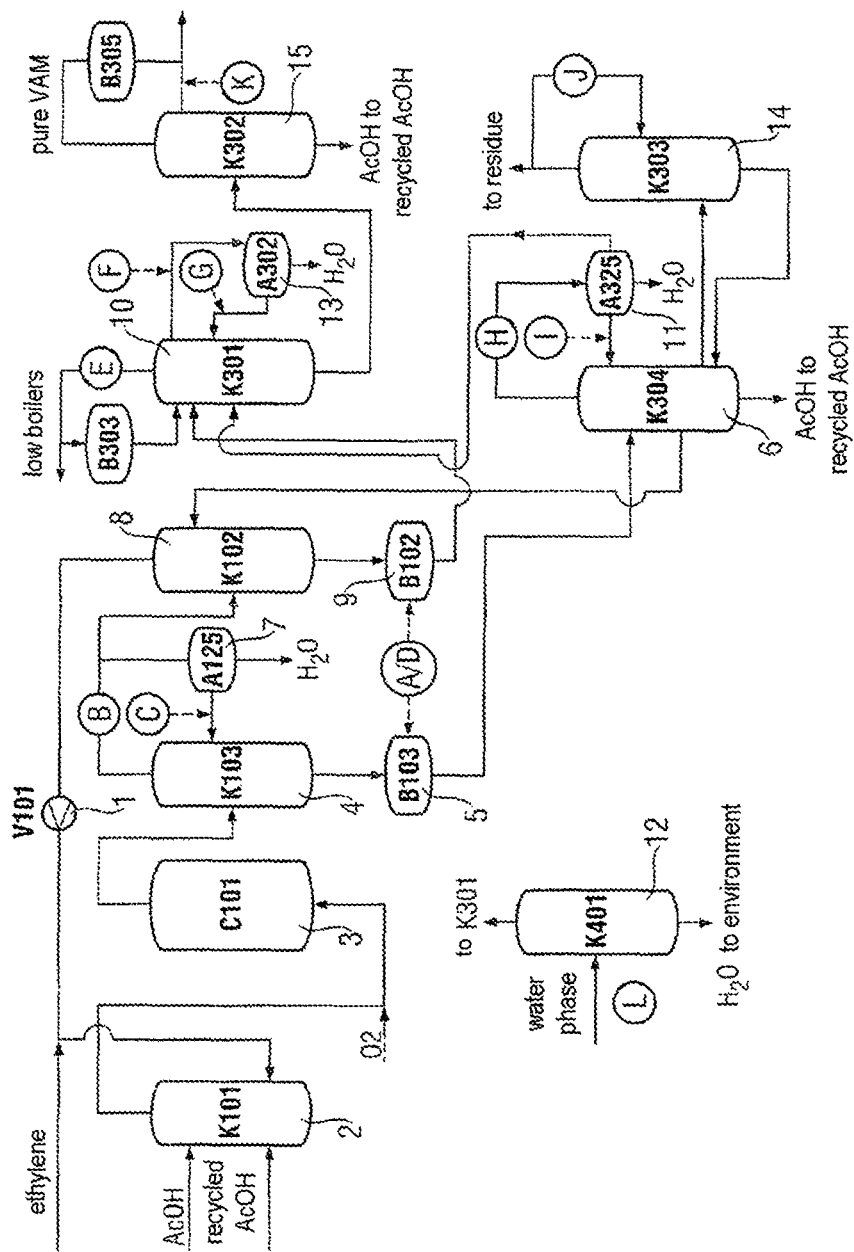

PROCESS FOR PREPARING VINYL ACETATE WITH INHIBITED BY-PRODUCT FORMATION

CROSS-REFERENCE TO RELATED APPLICATIONS

This application is a U.S. National Phase Application of PCT International Application PCT/EP2014/076210, filed Dec. 2, 2014 which claims priority to German Application No. 10 2013 225 114.9, filed Dec. 6, 2013, the contents of which are incorporated herein by reference in their entireties for all purposes.

The invention relates to a process for preparing vinyl acetate in a heterogeneously catalyzed, continuous gas phase process by reacting ethylene with acetic acid and oxygen and working up the product gas stream, wherein the by-product formation owing to the polymerization of vinyl acetate is inhibited in the course of workup of the product gas stream.

Vinyl acetate monomer (VAM) can be prepared in a continuous process with recycling of the purified product stream (cycle gas process). This involves reaction, in a heterogeneously catalyzed gas phase process, of ethylene with acetic acid and oxygen over catalysts which generally comprise palladium and alkali metal salts on a support material and may additionally be doped with gold, rhodium or cadmium. Preference is given to using a Pd/Au catalyst mixture with potassium acetate promoter.

The ethylene, oxygen and acetic acid reactants are converted in an exothermic reaction (VAM: $\Delta_R H°_{299}=-176$ kJ/mol), generally at a pressure of 7 to 15 bar gauge and, according to the service life of the catalyst, at a temperature of generally from 130° C. to 200° C., in a fixed bed tubular reactor, or else in fluidized bed reactors, to vinyl acetate:

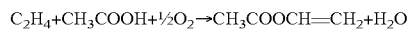

$$C_2H_4+CH_3COOH+\tfrac{1}{2}O_2 \rightarrow CH_3COOCH=CH_2+H_2O$$

The main side reaction is the total oxidation of ethylene to $CO_2$:

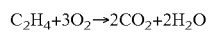

$$C_2H_4+3O_2 \rightarrow 2CO_2+2H_2O$$

The ethylene conversion is generally about 10%, the acetic acid conversion 20 to 30% and the oxygen conversion up to 90%.

In the preparation of vinyl acetate, therefore, because of the incomplete conversion of ethylene, a gas mixture consisting predominantly of ethylene, carbon dioxide, ethane, nitrogen and oxygen is circulated. The gas stream is admixed upstream of the fixed bed tubular reactor with the acetic acid, ethylene and oxygen reactants, and brought to reaction temperature with steam-operated heat exchangers. The cycle gas is typically enriched with acetic acid by means of a steam-heated acetic acid saturator.

After the reaction, the reaction products—vinyl acetate and water—and unconverted acetic acid are generally condensed out of the cycle gas in what is called a preliminary dewatering column and sent to further workup. Uncondensed product, essentially ethylene, $CO_2$ and vinyl acetate, is withdrawn at the top of the preliminary dewatering column and is extracted by scrubbing in an acetic acid-operated scrubber (cycle gas scrubber). The top product from the preliminary dewatering column (cycle gas) or at least a portion thereof is purified in a $CO_2$ scrubber to remove the carbon dioxide formed. The cycle gas is optionally compressed, admixed again with the reactants, and passed into the reactor for the gas phase oxidation.

For further workup of the condensate from the preliminary dewatering column, the condensed vinyl acetate and water products and unconverted acetic acid are separated from one another in a multistage distillation process typically operated with steam. The customary distillation steps for recovering the vinyl acetate and the acetic acid are dewatering column, azeotrope column, pure VAM column, residue workup, and low boiler and high boiler removal (see FIG. 1).

In the course of workup of the fractions comprising vinyl acetate, however, there is unwanted polymerization of the vinyl acetate monomer. This results in soiling and fouling in the individual columns, tubes and vessels of the workup process. The cleaning of the plant parts which is then necessary leads to a considerable loss of production efficiency. In the extreme case, it is even necessary to accept a halt to production. Furthermore, the VAM polymerization leads to product loss, i.e. a lower yield. The polymers also increase the viscosity of the by-product mixture which has to be removed as a viscous tar in any case. The processing and deposition of these tars then first requires a higher temperature and hence higher energy costs in the corresponding apparatus parts in order to transfer them into the corresponding disposal units. Subsequently, the problems in the individual plant parts or columns can then become so serious that a plant shutdown is unavoidable.

Established inhibitors for the polymerization of vinyl acetate are quinones and hydroquinones. DE-C 1244161 discloses the use of quinones for stabilizing vinyl acetate in the distillation. Even though the inhibitors mentioned are used in relatively high amounts of about 1000 to 2000 ppm, based on the amount of vinyl acetate, there is, repeatedly, unwanted polymerization, which gives rise to additional maintenance costs and in some cases leads to a continual reduction in plant throughput. EP 1233937 B1 recommends combinations of quinones with N-oxyl compounds for inhibiting the polymerization of unsaturated monomers, especially vinylaromatics, acrylic compounds and dienes. The use of hindered phenols such as 2,6-di-tert-butyl-4-nonylphenol as a fouling inhibitor in the production of vinyl acetate monomer in a cycle gas process is known from EP 567010 A1. The inhibitor, in solution in acetic acid, is added to the cycle gas before this gas is compressed for return to the reactor.

WO 97/46504 A1 discloses substance mixtures which comprise compounds containing vinyl groups, and a combination of 95.5 to 99.5% of a nitro compound and 0.05 to 4.5% of an N-oxyl compound. WO 98/25872 A1 discloses compositions comprising compounds containing vinyl groups, an N-oxyl compound of a secondary amine, and an iron compound. EP 791573 A1 prefers the use of 2,2,6,6-tetramethylpiperidinyloxyl (TEMPO), 4-oxo-TEMPO or the esters of 4-OH-TEMPO as inhibitor for the polymerization of VAM. Advice is given against using hydroxyl-functional or amino-functional N-oxyl compounds. WO 2007/045886 A1 recommends hydrophobic TEMPO compounds, especially ethers of 4-OH-TEMPO, as polymerization inhibitors for ethylenically unsaturated compounds. KR 10-2008-97529 recommends quinone compounds as polymerization inhibitors in gas phase oxidation, whereas TEMPO compounds are recommended for the workup of the cycle gas. WO 2012/058196 A1 provides a very general recommendation of radical scavengers for treating vinyl acetate compositions from the gas phase oxidation of ethylene and acetic acid. WO 2010/149527 A1 describes a process for preparing vinyl acetate by gas phase oxidation of ethylene and acetic acid, using N-oxyl compounds as polymerization inhibitors during the workup of the VAM-containing product stream.

It was therefore the object to configure the workup of the product gas stream from vinyl acetate production such that by-product formation owing to the polymerization of the vinyl acetate monomer is effectively inhibited.

N-oxyl compounds suitable for achieving this are generally six-membered cyclic N-oxyl compounds and are available commercially or can be prepared by processes known to those skilled in the art. The forms available commercially are solids or solutions thereof in vinyl acetate. In the last stage of the preparation of six-membered cyclic N-oxyl compounds, a secondary amine group is converted using hydrogen peroxide into the radical N-oxyl group. The reaction takes place in water and the reaction product is obtained in aqueous solution, at a high concentration of usually up to 80% by weight. With the products that are in commerce, the water is removed and the solid is purified, by means of multiple recrystallization, for example, and the pure N-oxyl compound is optionally dissolved in an organic solvent. To date, indeed, the assumption has been that without drying and purification, the efficacy and storage stability of N-oxyl compounds are inadequate.

Surprisingly it has now emerged that the inhibitor activity of the highly concentrated aqueous solution of the N-oxyl compounds originating from the last stage of synthesis or, generally, that of aqueous solutions of N-oxyl compounds is stable in storage and also, even more importantly, matches that achieved when using solids, or in the form of recrystallized solid, or in vinyl acetate solutions.

The invention provides a process for preparing vinyl acetate in a heterogeneously catalyzed, continuous gas phase process by reacting ethylene with acetic acid and oxygen and subsequently working up the product gas stream, with inhibition of the polymerization of vinyl acetate during the workup of the product gas mixture by addition of one or more N-oxyl compounds which contain at least one N-oxyl radical group —N—O. as inhibitors which comprises adding the N-oxyl compound as a 50 to 85% by weight strength aqueous solution.

N-oxyl compounds used are preferably those based on secondary amines in which the N-oxyl group is part of a saturated or unsaturated six-membered ring, for example piperidine-1-oxyl compounds, and in which each of the C atoms adjacent to the N-oxyl group bears two $C_1$- to $C_4$-alkyl groups, preferably methyl groups.

Particularly preferred six-membered cyclic N-oxyl compounds are 2,2,6,6-tetramethylpiperidinyloxyl (TEMPO), 4-hydroxy-2,2,6,6-tetramethylpiperidinyloxyl (4-OH-TEMPO), 4-oxo-2,2,6,6-tetramethylpiperidinyloxyl (4-oxo-TEMPO) and 4-ethanoyloxy-2,2,6,6-tetramethylpiperidinyloxyl. Most preferred are 2,2,6,6-tetramethylpiperidinyloxyl (TEMPO) and 4-hydroxy-2,2,6,6-tetramethylpiperidinyloxyl (4-OH-TEMPO).

The N-oxyl compound is used generally as a 50 to 85% by weight, preferably 75 to 85% by weight, strength aqueous solution. The highly concentrated aqueous solution obtained during the synthesis of the N-oxyl compounds, and optionally not purified further from the last stage, is preferably used as it is as an inhibitor in the process of the invention for preparing vinyl acetate. The N-oxyl compound may also be used in a water/vinyl acetate mixture. Preference is given to using the N-oxyl compound alone and not in combination with other additives, in aqueous solution or in solution in a water/vinyl acetate mixture.

The amount of N-oxyl compound required for the process depends firstly on the construction and capacity of the particular plant. The amount required can be determined by monitoring and analysis of the streams in the plant, i.e. by means of quantitative determination of the total polymer formation or polymer formation in individual plant parts. The amount used also depends on whether the aim of using the N-oxyl compound is a prophylactic treatment to extend the service life of the overall plant, or to inhibit the occurrence of polymer in individual plant parts, in order there to reduce the treatment cost and labor for the cleaning.

In general, use amounts of 50 to 500 ppm, preferably 50 to 200 ppm, of N-oxyl compound, in each case per tonne of vinyl acetate in the product gas stream, are sufficient for the entire plant. This use amount can be added at one point or distributed over two or more points in the plant for working up the product gas stream, i.e. in one or more columns, lines or reservoir vessels.

Preferred points A to L for addition of the inhibitor are shown in FIG. 1.

FIG. 1 shows a simplified scheme for the preparation of vinyl acetate in a gas phase process and subsequent workup of the product gas stream.

The cycle gas compressed with the cycle gas compressor V-101 (1) is enriched with fresh ethylene, which replaces the ethylene content consumed in the reaction, and supplied to the acetic acid saturator K-101 (2). The acetic acid converted in the reaction is replaced in the acetic acid saturator (2) by infeed of fresh acetic acid. The high boilers and other by-products, for example all recycled polymers and unconsumed inhibitors, are drawn off at the bottom of the acetic acid saturator (2) and freed of residual acetic acid in the acetic acid workup, and the remaining residues are disposed of.

Since the acetic acid is converted incompletely in the reaction, this acetic acid is drawn off at the bottom in each of the downstream distillations (for example, in (6) and (15)) and supplied to the recycled acetic acid tank.

Before the acetic acid-laden cycle gas leaving the acetic acid saturator K-101 (2) enters the reactor system, oxygen is added to it via a nozzle. Subsequently, the cycle gas is supplied with a cycle gas pressure of 7 to 15 bar abs. to the fixed fed tubular reactor C-101 (3) which is laden with a Pd/Au catalyst mixture with potassium acetate promoter and is operated at a temperature of 130 to 200° C.

The gas stream leaving the fixed bed tubular reactor C-101 (3) is supplied to the lower part of the preliminary dewatering column K-103 (4). A first condensate (vinyl acetate, water and unreacted acetic acid) from this column is passed into the crude VAM vessel B-103 (5). The crude VAM vessel B-103 (5) is point A at which the inhibitor can be metered in.

The crude VAM from the crude VAM vessel B-103 (5) is then pumped into the azeotrope column K-304 (6). The main gas stream from the preliminary dewatering column K-103 (4) can be inhibited upstream of the subsequent condensation in the cycle gas scrubber K-102 (8) (point B). To inhibit the return stream from the phase separator A-125 (7), the N-oxyl compound can be added on the way to the preliminary dewatering column K-103 (4) (point C).

The uncondensed constituent of the top vapors of the preliminary dewatering column (4), essentially ethylene, $CO_2$ and vinyl acetate, is released to the cycle gas scrubber K-102 (8). The uncondensed VAM fractions are absorbed in the acetic acid-operated cycle gas scrubber K-102 (8). The absorption AcOH required for the cycle gas scrubbing can be supplied from the azeotrope column K-304 (6). The now VAM-free cycle gas is supplied via the cycle gas compressor V-101 (1) and the acetic acid saturator K-101 (2) back to the reaction in the reactor C-101 (3). The bottom product from the cycle gas scrubber K-102 (8) is passed into the crude VAM vessel B-102 (9) and from there into the dewatering column K-301 (10). Inhibitor can likewise be added to the crude VAM vessel B-102 (9) and/or to the crude VAM vessel B-103 (5) (point D).

Preferably a second crude VAM stream is generally also passed into the dewatering column K-301 (10): the crude VAM from the crude VAM vessel B-103 (5) (=condensate from preliminary dewatering (4)). This is first distilled in the azeotrope column K-304 (6). The top product of this distillation in the azeotrope column K-304 (6), essentially vinyl acetate and water, is transferred to the phase separator A-325 (11) for water removal, and can be admixed with inhibitor between azeotrope column (6) and phase separator (11) (point H).

The majority of the organic phase (essentially VAM) from the phase separator A-325 (11) is pumped as the return stream back into the azeotrope column K-304 (6) and can be inhibited beforehand (point I). The remaining portion of the organic phase is transferred to the dewatering column K-301 (10).

The aqueous phase of the phase separator A-325 (11) is delivered to the wastewater column K-401 (12), in which all aqueous phases from the phase separators A-125 (7), phase separator A-302 (13) and phase separator A-325 (11) of the overall distillation are worked up. The aqueous bottom product from the wastewater column (12) is disposed of, and the top product recycled into the dewatering column K-301 (10). For inhibition, the inhibitor can be fed into the wastewater column K-401 (12) at the inlet of the aqueous phases (point L).

To remove the ethyl acetate, a side draw from the azeotrope column K-304 (6) can be passed to the ethyl acetate column K-303 (14). Inhibitor can likewise be metered in the return stream of this ethyl acetate column K-303 (14) (point J).

In the dewatering column K-301 (10), preferably, essentially the bottom product from the cycle gas scrubber K-102 (8), which comprises essentially water, vinyl acetate, acetic acid and low boilers (in particular acetaldehyde), is separated: the low boilers and water are removed from vinyl acetate and acetic acid. The acetaldehyde which has been formed here by vinyl acetate hydrolysis is removed via the top of the dewatering column K-301 (10), then condensed and pumped to the further workup. At this point, inhibitor can be added (point E).

An intermediate tray of the dewatering column K-301 (10) can be used to pass the aqueous side draw to the phase separator A-302 (13). Inhibitor can be added at this line (point F). The organic phase is optionally inhibited (point G) and then, optionally at more than one point, fed back as return stream to the dewatering column K-301 (10).

The bottom product of the dewatering column K-301 (10), vinyl acetate and acetic acid, is passed to the pure VAM column K-302 (15). Pure VAM is removed via the top and partly recycled as the return stream. Inhibitor can likewise be added to this return stream (point K). The bottom product, essentially acetic acid, is fed to the acetic acid workup.

In this scheme in FIG. 1, the $CO_2$ scrubbing and the acetic acid workup are not described, since only small amounts, if any, of vinyl acetate are present in the corresponding process steps, and therefore no inhibitor addition is generally required there.

Surprisingly it has been possible to show that the use of an aqueous solution coming directly from the synthesis of the N-oxyl compound had distinct advantages over the use of hydroquinone (see comparative example 1).

The examples which follow serve to further illustrate the invention:

In a plant according to FIG. 1, which was operated under the abovementioned conditions (cycle gas pressure 7 to 15 bar abs., reaction temperature 130 to 200° C.) with a gas hourly space velocity (GHSV) of approx. 3000 to 4000 [1/h] and a space-time yield (STY) of 600 to 1200 (kg VAM/m$^3$ cat×h), inhibitor was added at each of points A to L.

Samples were taken from the bottoms of the following columns for analysis, and the polymer formation in the columns was analyzed quantitatively:

azeotrope column K-304 (6); dewatering column K-301 (10) and pure VAM column K-302 (15).

Comparative Example 1

First, a total of 1300 to 2100 ppm of hydroquinone per tonne of VAM were added at points A to L over a period of one month.

After one month, the following polymer formation rates were measured in the columns:

Dewatering column K-301 (11): 20-50 kg/h
Pure VAM column K-302 (16): 5-8 kg/h
Azeotrope column K-304 (9): 15-20 kg/h Example 1

After comparative example 1 had expired, a total of 50 to 200 ppm of 4-hydroxy-2,2,6,6-tetramethylpiperidine 1-oxyl (4-OH-TEMPO) per tonne of VAM were added at points A to L over a period of a further month, in each case as a 75% by weight strength aqueous solution.

After the month of inhibition with the aqueous OH-TEMPO solution had expired, the following polymer formation rates were measured in the columns:

Dewatering column K-301 (11): 10-20 kg/h
Pure VAM column K-302 (16): 1-3 kg/h
Azeotrope column K-304 (9): 8-10 kg/h Example 2

After example 1 had expired, a total of 50 to 200 ppm of 2,2,6,6-tetramethylpiperidine 1-oxyl (TEMPO) per tonne of VAM were added at points A to L over a period of a further month, in each case as a 75% by weight strength aqueous solution.

After the month of inhibition with the aqueous TEMPO solution had expired, the following polymer formation rates were measured in the columns:

Dewatering column K-301 (11): 11-22 kg/h
Pure VAM column K-302 (16): 2-4 kg/h
Azeotrope column K-304 (9): 10-12 kg/h In spite of the significantly smaller amounts of TEMPO and 4-OH-TEMPO used, and in spite of their being used in highly concentrated aqueous solution form, significantly more effective inhibition of polymer formation was achieved compared to one month of inhibition with hydroquinone.

The invention claimed is:

1. A process for preparing vinyl acetate in a heterogeneously catalyzed, continuous gas phase process by reacting ethylene with acetic acid and oxygen and subsequently working up the product gas stream, with inhibition of the polymerization of vinyl acetate during the workup of the product gas mixture by addition of one or more N-oxyl compounds which contain at least one N-oxyl radical group —N—O. as inhibitors which comprises adding the N-oxyl compound as a 50 to 85% by weight strength aqueous solution, wherein the aqueous solution of the N-oxyl compound that is used is the aqueous solution obtained in the synthesis of the N-oxyl compound.

2. The process as claimed in claim 1, wherein N-oxyl compounds added are those from the group of secondary amines in which the N-oxyl group is part of a saturated or unsaturated six-membered ring, and in which each of the C atoms adjacent to the N-oxyl group bears two C1- to C4-alkyl groups.

3. The process as claimed in claim 1, wherein the N-oxyl compound added comprises 2,2,6,6-tetramethylpiperidinyloxyl, 4-hydroxy-2,2,6,6-tetramethylpiperidinyloxyl, 4-oxo-2,2,6,6-tetramethylpiperidinyloxyl and/or 4-ethanoyloxy-2,2,6,6-tetramethylpiperidinyloxyl.

4. The process as claimed in claim 1, wherein the N-oxyl compounds are used in a water/vinyl acetate mixture.

5. The process as claimed in claim 1, wherein 50 to 500 ppm of N-oxyl compound are added per tonne of vinyl acetate in the product gas stream.

6. The process as claimed in claim 1, wherein the N-oxyl compound is added at one point or distributed over two or more points in the plant for working up the product gas stream.

7. The process as claimed in claim 5, wherein the N-oxyl compound is added
- to the condensate from a preliminary dewatering column and/or
- to a gas stream from the preliminary dewatering column and/or
- to a return stream to the preliminary dewatering column and/or
- to a bottom product from a cycle gas scrubber and/or
- to a top product of an azeotrope column and/or
- to a return stream into the azeotrope column and/or
- to the inlet into a wastewater column and/or
- to a return stream into an ethyl acetate column and/or
- to a top product of a dewatering column and/or
- to a side draw of the dewatering column and/or
- to a return stream into the dewatering column and/or
- to a top product of a pure vinyl acetate column.

* * * * *